US00PP16461P2

(12) United States Plant Patent
Bradford

(10) Patent No.: US PP16,461 P2
(45) Date of Patent: Apr. 18, 2006

(54) INTERSPECIFIC TREE NAMED 'PLUMSWEET IV'

(50) Latin Name: ***Prunus salicina*×sp.**
Varietal Denomination: Plumsweet IV

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 107 days.

(21) Appl. No.: 11/029,693

(22) Filed: Jan. 6, 2005

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP12,097 P2 * 9/2001 Zaiger et al. ..... Plt./180
PP13,458 P2 1/2003 Bradford
PP14,219 P2 * 10/2003 Bradford ..... Plt./184

* cited by examiner

*Primary Examiner*—Anne Marie Grunberg
*Assistant Examiner*—W. C. Haas

(57) ABSTRACT

The present invention relates to an interspecific tree and more particularly to a new and distinct variety broadly characterized by large size, vigorous, hardy, and self-unfruitful but productive tree. The fruit matures under the ecological conditions described during mid September, with first picking on Sep. 15, 2003, and will hang on the tree for nearly twenty more days. The fruit is uniformly large in size, red over a greenish yellow background in skin color, clingstone in type, somewhat oblong in shape, yellow with some red bleeding in flesh color, very firm and crisp in texture, and outstanding in flavor.

1 Drawing Sheet

CROSS-REFERENCE TO RELATED APPLICATIONS

The present application is related to co-pending U.S. Plant patent application Ser. No. 11/029,689.

Botanical classification: *Prunus salicina*×sp.

Varietal denomination: 'Plumsweet IV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet IV'.

During a typical blooming season I isolate as seed parents both individual and groups of different plum trees by covering them with screen houses. A hive of bees is placed inside each such house and bouquets to provide pollen from different plum, apricot, and interspecific plum-apricot hybrid trees are placed near the trees approximately every two days for the duration of the bloom. During 1997 one such house containing an unnamed red plum was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "38PH9". They were grown as seedlings on their own root in my greenhouse and, upon reaching dormancy, transplanted to a cultivated area of my experimental orchard at Bradford Farms near Le Grand, Calif. in Merced County (San Joaquin Valley). During the summer of 2001 the present variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is quite similar to 'YUMMYgiant' (U.S. Plant Pat. No. 13,458) plum by being self-unfruitful and by producing fruit that is large in size, oblong in shape, and clingstone in type, but is distinguished therefrom by producing fruit that is sweeter in flavor, that is firmer in texture, that matures about 45 days later, and that has a less percentage of red skin color with more yellow green background color present.

SUMMARY OF VARIETY

The present interspecific fruit variety is characterized by a large size, vigorous, hardy, and productive tree. Being self-unfruitful, the present variety requires cross pollination from a plum that blooms during the mid season, such as 'Plumsweetone' (U.S. Plant Pat. No. 14,219). The present variety's abundance of blossoms and pollen entices strong bee activity to facilitate pollination. The fruit matures under the ecological conditions described during mid September, with first picking on Sep. 15, 2003, and will hang on the tree for nearly twenty more days. The fruit is uniformly large in size, red over a greenish yellow background in skin color, clingstone in type, somewhat oblong in shape, yellow with some red bleeding in flesh color, very firm and crisp in texture, and outstanding in flavor.

DRAWING

The accompanying photograph consists of four whole fruits positioned to display the characteristics of the skin color and form, two halves of one fruit divided transversely to the suture plane to reveal the flesh and stone, typical leaves and an inset depicting the blossoms as they appear on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Sep. 15, 2003, on the original tree during its sixth growing season. The flower and bud descriptions were developed the following blooming season. All major color code designations are by reference to the Inter-Society Color Council, National Bureau of Standards. Common color names are also used occasionally.

Tree

Size: Large, reaching and maintaining a height of 14' [4.3 m.] and a spread of 8' [2.4 m.] after six growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum, such as 'Plumsweetone' (U.S. Plant Pat. No. 14,219).

Bearing: Regular bearer.

Trunk:

*Size.*—Medium, reaching a maximum diameter of 4⅜" [111 mm.] after the sixth growing season.

*Texture.*—Shaggy.

*Bark color.*—A Dark reddish brown [44. d.rBr] and Moderate reddish brown [43. m.rBr] variegation with Light orange yellow [70. l.OY] crevices present.

*Lenticels.*—Approximate Number Per Square Inch: 18. Color: Moderate orange [53. mO]. Typical Size: ⅛" [3.2 mm.] to ⅜" [9.5 mm.]. Shape: Eye-shaped to elongated.

Branches:

*Size.*—Diameter of limb is 2¼" [57 mm.] measured 12" above first fork, and dependent upon cultural practices and climatic conditions.

*Texture.*—Shaggy.

*Color.*—1st Year Wood Topside: Moderate brown [58. m.Br]. 1st Year Wood Underside: Brilliant yellow green [116. brill.YG]. Older Wood: A Grayish Brown [61. gy.Br] and Light yellowish brown [76. l.yBr] variegation.

*Lenticels.*—Number Per Square Inch: More than 80 on second year wood. Color: Light orange yellow [70. l.OY]. Typical size: 1/32" [0.76 mm.]. Shape: Eye-shaped to elongated.

Leaves:

*Size.*—Medium. Average Length: 4½" [114 mm.]. Average width: 1⅞" [48 mm.].

*Arrangement.*—Alternate.

*Thickness.*—Medium.

*Form.*—Elliptical.

*Apex.*—Acuminate.

*Base.*—Acute, with an average base angle of 50 degrees.

*Surface.*—Smooth.

*Color.*—Dorsal Surface: Moderate olive green [125. m.OlG]. Ventral Surface: Moderate yellow green [120 m.YG].

*Margin.*—Finely serrate.

*Venation.*—Pinnately net veined.

*Petiole.*—Average Length: ⅞" [22.2 mm.]. Average Thickness: 1/16" [1.6 mm.]. Color: Moderate yellow green [120. m.YG].

*Stipules.*—Number: Usually 2 per leaf. Average Length: ¼" [6.4 mm.]. Color: Light yellow green [119. l.YG].

*Glands.*—Number: 0 to 4 observed, average 2. Position: Both alternate and opposite, observed to be on petiole and/or base of blade, no definitive pattern. Size: Small. Form: Globose. Color: Light yellow green [119. l.YG] with Grayish reddish brown [46. gy.rBr] centers increasing with age.

*Leaf buds.*—Small, conic and pointed.

Flower buds:

*Hardiness.*—Hardy, with respect to central California winters.

*Diameter.*—Typically 3/16" [4.8 mm.] 3 days before bloom.

*Length.*—Typically ⅜" [9.5 mm.] 3 days before bloom.

*Form.*—Not appressed.

*Surface.*—Pubescent.

*Color.*—White [263. White].

Flowers: Perfect, complete, perigynous, usually a single pistil, typically thirty or more stamens, five sepals and petal locations alternately positioned.

*Average flower diameter.*—15/16" [23.8 mm.].

*Number of petals.*—Five, no double blossoms observed.

*Petal shape.*—Oval to slightly obovate.

*Petal margin.*—Very wavy.

*Average petal diameter.*—5/16" [7.9 mm.].

*Average petal length.*—7/16" [11.1 mm.].

*Petal apex.*—Rounded.

*Petal base.*—Rounded to somewhat cuneate.

*Petal color.*—White [263. White].

*Anther color.*—Light yellow [86. l.Y].

*Stigma color.*—Pale greenish yellow [104. p.gY].

*Sepal color.*—Light yellow green [119. l.YG].
*Sepal length.*—5/32" [4.0 mm.].
*Sepal width.*—1/8" [3.2 mm.].
*Average pistil length.*—3/8" [9.5 mm.].
*Average stamen length.*—3/8" [9.5 mm.].
*Fragrance.*—Moderate.
*Pollen production.*—Abundant.
*Blooming period.*—Medium compared with other varieties, with 'Santa Rosa' (unpatented).
*Onset of bloom.*—One percent on Feb. 28, 2004.
*Date of full bloom.*—Mar. 9, 2004.
*Duration of bloom.*—One to two weeks, dependent on ambient temperature.
*Number per cluster.*—2 to 10, average 5.

FRUIT

Maturity when described: Full ripe, Sep. 28, 2003.
Date of first picking: Sep. 15, 2003.
Date of last picking: Oct. 5, 2003.
Size: Uniform, large.
*Average diameter axially.*—2¾" [69.9 mm.].
*Average diameter across suture plane.*—2⅝" [66.7 mm.].
*Typical weight.*—6.8 ounces [193 grams].
Form: Somewhat oblong, slightly asymmetrical.
*Longitudinal section form.*—Somewhat oval.
*Transverse section through diameter.*—Circular.
Suture: A shallow groove extending from the stem cavity to the apex.
Ventral surface: Rounded.
Lips: Very slight, fairly equal.
Cavity: Flaring, circular, suture showing on one side.
*Depth.*—7/16" [11.1 mm.].
*Breadth.*—13/16" [20.6 mm.].
Base: Rounded to somewhat truncate.
Apex: Rounded to slightly mammiform on some.
Pistil point: An inconspicuous Grayish brown [61. gy.br] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to flesh.
*Astringency.*—Slightly astringent.
*Tendency to crack.*—Slight in dry season.
*Color.*—Deep red [13. deep R] mottled over a Grayish yellow [90. gy.Y] background, a Moderate yellow [87. m.Y] stripe located along the suture, Pale yellowish green [104. p.gY] freckling throughout.
*Bloom.*—Abundant.
Flesh:
*Color.*—Pale yellow [89. p.Y] toward the stone with a Dark red [16. d.R] ¼" [6.4 mm] layer toward the skin, becoming much darker and thicker with maturity.
Surface of pit cavity.—Clingstone with Brownish pink [33. br.Pk] fibers breaking when twisted from stone.
*Amygdalin.*—Moderate.
*Juice.*—Abundant, rich.
*Texture.*—Firm and crisp.
*Fibers.*—Abundant, tough.
*Ripens.*—Slightly earlier at apex.
*Flavor.*—Mildly acidic and abundantly sweet, 22 to 26 brix.
*Aroma.*—Slight.
*Eating quality.*—Very best.

STONE

Type: Clingstone.
Form: Oval.
Hilum: Narrow, oblong.
Base: Characteristically notched.
Apex: Acuminate with a very sharp 1/8" [3.2 mm] tip.
Sides: Equal.
Surface: Rough, with a single groove from the base to apex on each side of the dorsal fin.
External color of stone: Moderate yellowish brown [77. m.yBr].
Pit wall color when cracked: Moderate brown [58. m.Br].
Cavity surface color: Light brown [57. l.Br] with some Dark brown [59. d.Br] areas.
Average pit wall thickness: 1/16" [1.6 mm.].
Average width: 11/16" [17.5 mm.].
Average length: 1¼" [31.8 mm.].
Average breadth: 3/8" [9.5 mm.].
Tendency to split: None observed.
Kernel:
*Form.*—Oval.
*Skin color.*—Dark orange yellow [72. d.OY].
*Pellicle color.*—Dark yellowish brown [78. d.yBr].
*Vein color.*—Moderate yellowish brown [77. m.yBr].
*Taste.*—Bitter.
*Viable.*—Yes.
*Average width.*—½" [12.7 mm.].
*Average length.*—11/16" [17.5 mm.].
*Amygdalin.*—Abundant.

USE

Market: Fresh market and long distance shipping.
Keeping quality: Marginal, as fruit texture, juice, flesh color, and flavor observed to remain in good condition for 30 days in standard cold room at 36° Fahrenheit [2° Celsius], however wrinkling in the shoulder area occurs within 14 days.
Shipping quality: Average.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* tree, substantially as illustrated and described, that is similar to 'YUMMYgiant' (U.S. Plant Pat. No. 13,458) plum by being self-unfruitful and by producing fruit that is large in size, oblong in shape, and clingstone in type, but is distinguished therefrom by producing fruit that is sweeter in flavor, that is firmer in texture, that matures about 45 days later, and that has a less percentage of red skin color with more yellow green background color present.

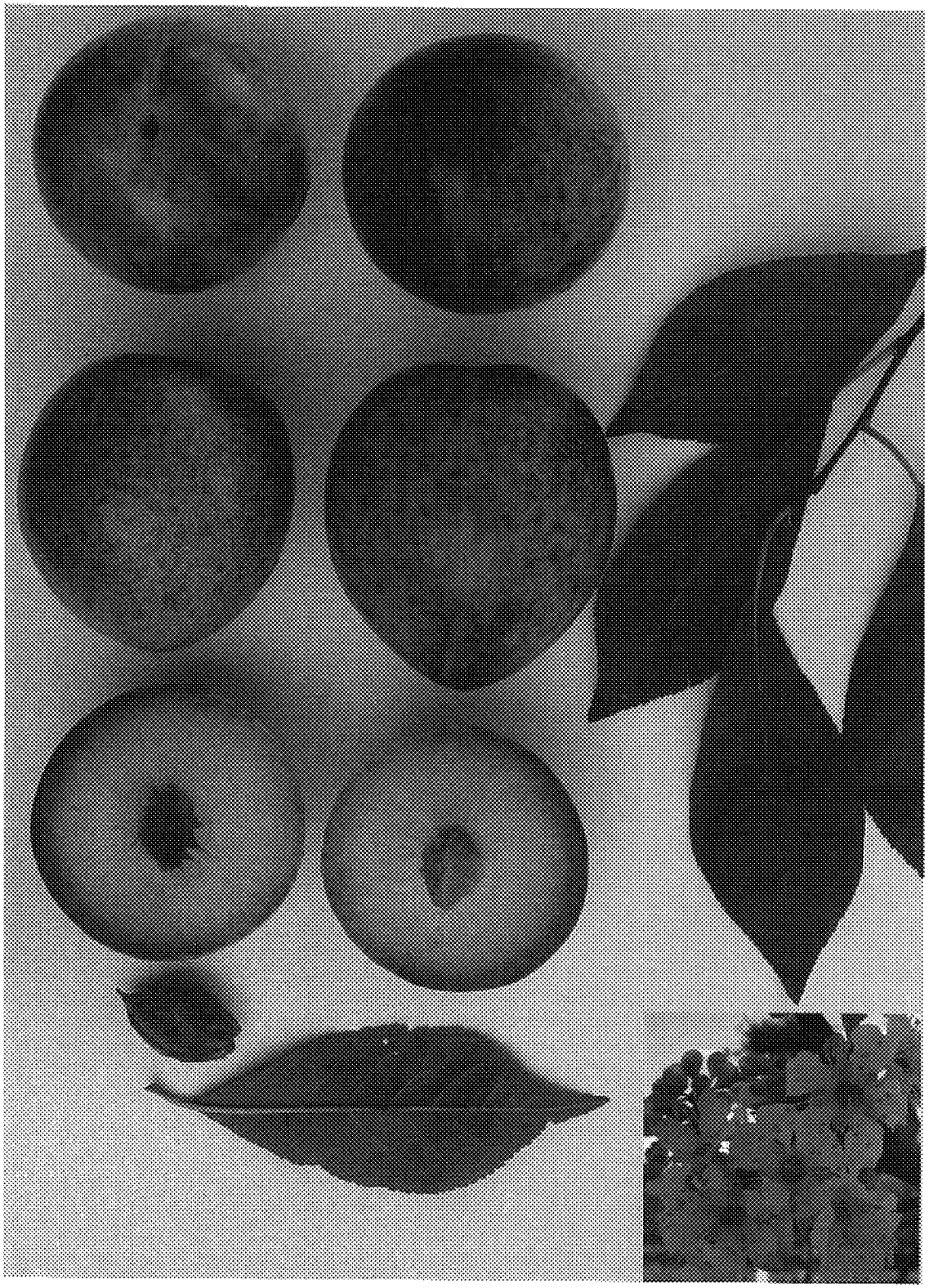

* * * * *